(12) United States Patent
Böhme et al.

(10) Patent No.: US 11,298,015 B2
(45) Date of Patent: Apr. 12, 2022

(54) ILLUMINATING SYSTEM FOR DETERMINING THE TOPOGRAPHY OF THE CORNEA OF AN EYE

(71) Applicant: Carl Zeiss Meditec AG, Jena (DE)

(72) Inventors: Beate Böhme, Großpürschütz (DE); Rico Fuchs, Jena (DE); Günter Rudolph, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 157 days.

(21) Appl. No.: 16/330,079

(22) PCT Filed: Aug. 31, 2017

(86) PCT No.: PCT/EP2017/071823
§ 371 (c)(1),
(2) Date: Mar. 2, 2019

(87) PCT Pub. No.: WO2018/041926
PCT Pub. Date: Mar. 8, 2018

(65) Prior Publication Data
US 2019/0246899 A1    Aug. 15, 2019

(30) Foreign Application Priority Data
Sep. 2, 2016    (DE) ...................... 10 2016 216 615.8

(51) Int. Cl.
*A61B 3/107* (2006.01)
*A61B 3/00* (2006.01)
(Continued)

(52) U.S. Cl.
CPC ............ *A61B 3/107* (2013.01); *A61B 3/0008* (2013.01); *G01B 11/2513* (2013.01); *A61B 3/103* (2013.01); *A61B 3/1005* (2013.01)

(58) Field of Classification Search
CPC ..... A61B 3/107; A61B 3/0008; A61B 3/1005; A61B 3/103; G01B 11/2513
(Continued)

(56) References Cited

U.S. PATENT DOCUMENTS 4,837,588 A * 6/1989 Imakawa ............. H04N 1/0281
347/250
5,439,621 A    8/1995 Hoopman
(Continued)

FOREIGN PATENT DOCUMENTS

CN    201522557 U    7/2010
DE    103 33 558 A1    3/2005
(Continued)

OTHER PUBLICATIONS

International Search Report and Written Opinion for International Application No. PCT/EP2017/071823, dated Dec. 21, 2017, 13 pages.
(Continued)

*Primary Examiner* — Marin Pichler
*Assistant Examiner* — Mitchell T Oestreich
(74) *Attorney, Agent, or Firm* — Patterson Thuente Pedersen, P.A.

(57) ABSTRACT

An illumination system for producing an illumination pattern for measuring the cornea of an eye and, in particular, for determining the topography thereof and in so doing facilitating distance-independent measurements. The illumination system according to the invention for determining the topography of the cornea of an eye includes an illumination unit and a unit for producing an illumination pattern, wherein the illumination unit includes a plurality of illumination modules. A lens array which produces a spatially distributed, collimated illumination pattern is used as a unit for producing an illumination pattern. The illumination system pro-
(Continued)

duces an illumination pattern, by which the topography of the cornea of an eye can be determined. Here, the illumination system is designed as a compact module, and so it can be easily combined with other measurement systems, without colliding with the beam paths thereof.

19 Claims, 3 Drawing Sheets

(51) Int. Cl.
G01B 11/25 (2006.01)
A61B 3/103 (2006.01)
A61B 3/10 (2006.01)

(58) Field of Classification Search
USPC .......................................................... 351/121
See application file for complete search history.

(56) References Cited

U.S. PATENT DOCUMENTS

| | | | |
|---|---|---|---|
| 6,212,011 B1 | 4/2001 | Lissotschenko et al. | |
| 6,464,362 B1 | 10/2002 | Sugawara et al. | |
| 6,779,891 B1 | 8/2004 | Barth | |
| 7,374,287 B2 * | 5/2008 | Van de Velde | A61B 3/102 351/221 |
| 2005/0018137 A1 * | 1/2005 | Barth | A61B 3/0025 351/221 |
| 2014/0320819 A1 * | 10/2014 | Muller | A61B 3/0008 351/221 |

FOREIGN PATENT DOCUMENTS

| | | |
|---|---|---|
| DE | 10 2006 010105 A1 | 8/2007 |
| DE | 10 2011 102 354 A1 | 11/2012 |
| DE | 10 2011 102 355 A1 | 11/2012 |
| DE | 10 2011 106 288 A1 | 1/2013 |
| DE | 10 2012 019 474 A1 | 4/2014 |

OTHER PUBLICATIONS

German Search Report for Application No. 10 2016 216 615.8, dated Apr. 12, 2017, 10 pages.
English translation of International Search Report for International Application No. PCT/EP2017/071823, dated Dec. 21, 2017, 3 pages.
English translation of International Report on Patentability for PCT International Search Report and Written Opinion for International Application No. PCT/EP2017/071823, dated Mar. 14, 2019, 8 pages.

* cited by examiner

ILLUMINATING SYSTEM FOR DETERMINING THE TOPOGRAPHY OF THE CORNEA OF AN EYE

RELATED APPLICATIONS

This application is a National Phase entry of PCT Application No. PCT/EP2017/071823 filed Aug. 31, 2017, which application claims the benefit of priority to DE Application No. 10 2016 216 615.8, filed Sep. 2, 2016, the entire disclosures of which are incorporated herein by reference.

TECHNICAL FIELD

The present invention relates to an illumination system for producing an illumination pattern for measuring the cornea of an eye and, in particular, for determining the topography thereof. In so doing, facilitates distance-independent measurements.

BACKGROUND

While the term keratometry should be understood to mean measuring the shape and form of the cornea of the eye, the central and peripheral radii of curvature of the cornea are measured and evaluated mathematically by specific methods within the scope of topography as a special form of keratometry.

Historically, measuring the surface of the cornea of the human eye was found difficult to the effect that the cornea is transparent and visible light is not scattered back to any note-worthy extent.

Methods for measuring the corneal surface shape with the aid of so-called keratometers or keratographs has long been known according to the prior art. The concentric rings of a so-called Placido disk that are imaged onto the cornea are reflected by the tear film of the cornea and are recorded and evaluated using a camera. The reflected ring pattern detected by the camera is distorted depending on the curvature of the cornea.

The Placido disk is an illuminated disk, on which round circles are applied at regular intervals. Then, the diagnosis is on the basis of the observed reflections of the circles on the surface of the cornea, on which the circles should likewise be imaged in regular fashion. In so doing, all that should be seen now on the corneal surface is a symmetric reflection of the concentric Placido circles. By contrast, if asymmetric forms of the circles can be found, these are indications for a deviation of the corneal surface from a reference surface. Irregularities in the corneal surface can be found in the case of an astigmatism, for example, but also in the case of mechanical or chemical injuries of the cornea.

Commercially available topography systems project real Placido rings at a small distance in front of the eye onto the cornea, from where they are reflected and captured by a camera. The corneal reconstruction is based on the angular evaluation of the angle of incidence and angle of reflection of the projected Placido rings which are reflected by the cornea. Here, the deviation of the ring position on the cornea relative to the ring position of a known reference test body serves as a basis for the corneal reconstruction. A second disadvantage of such solutions can be seen in the fact that the accuracy of the measurement depends strongly on the angle relationships, and hence on the measurement distance.

Very different methods are used for determining or checking the correct measurement distance. By way of example, the measurement can be triggered automatically when the correct working distance has been reached. Firstly, this can be implemented by correcting the erroneous distance before each measurement by virtue of the distance or the position being determined with the aid of photoelectric barriers, contacts or additional measurement systems, and being corrected where necessary.

By contrast, other solutions known from the prior art are based on distance-independent measurement and a telecentric detection for determining the topography of the cornea of an eye.

DE 10 2011 102 355 A1 describes a system for topography, in which the light of a light source is collimated by means of an aspherical surface and directed onto the eye via a Fresnel axicon illuminated over the entire area thereof. Furthermore, the solution contains a light source on the optical axis and elements for output coupling the measurement radiation. In this solution, small illumination angles are produced by small deflection angles on refractive surfaces, whereas large deflection angles have to be realized by additional reflective surfaces.

A disadvantage of this solution lies in the use of reflective surfaces in the material since surface defects in this case have a substantially stronger effect on the collimation of the incident light than in the case of refractive surfaces. Furthermore, the beams extend between the light source and collimation optical unit in divergent fashion, and so smaller free diameters are available in this installation space for other components than between the collimation optical unit and Fresnel axicon.

For the purposes of measuring the corneal curvature, the return reflections from the cornea have to be output coupled onto an imaging system in addition to the illumination. However, if the installation space is blocked by the illumination cone, output coupling can only be implemented further downstream or laterally, increasing the complexity, installation size and costs of the overall appliance.

The smaller free diameters present in the installation space also lead to a modular use of the solution, for example in conjunction with a biometric measurement arrangement, being made more difficult or even prevented as a result of possible collisions of the coaxial illumination with other beam paths.

Furthermore, it is found to be disadvantageous that the relatively large deflection angles require low manufacturing tolerances, particularly in the case of the reflective facets. Moreover, a uniform illumination can hardly be achieved.

The system described in DE 10 2011 102 354 A1 for determining the surface shape of the cornea of an eye is based on a specific Placido disk with telecentric image evaluation. The Placido disk comprises halved, toroidal elements with a semicircular cross section, which have different radii and the front, spherical or aspherical surfaces of which are directed to the cornea of the eye. The Placido disk is illuminated by way of LEDs, which are respectively arranged in the focus of the halved, toroidal elements in order to realize the projection of the rings of the Placido disk to infinity in the direction of the cornea of the eye. Although this has solved the problem of fewer free diameters by virtue of the LEDs being arranged directly on the Placido disk, the manufacture and adjustment was found to be extremely complicated and difficult.

SUMMARY OF THE INVENTION

Example embodiments of the invention include an illumination system for producing an illumination pattern for measuring the topography of the cornea of an eye which facilitates distance-independent measurements. In the illumination system according to example embodiments of the invention, the region around the optical axis of the system can be kept free for further system components. Moreover, the illumination system includes individual components whose tolerances and manufacturing errors have little effect in the overall system such that these are easily producible.

According to an example embodiment, the illumination system for determining the topography of the cornea of an eye, includes an illumination unit and a unit for producing an illumination pattern, by virtue of the illumination unit consisting of a plurality of illumination modules and the unit for producing an illumination pattern which produces a spatially distributed, collimated illumination pattern.

The inventive illumination system serves to produce an illumination pattern, by use of which the topography of the cornea of an eye can be determined. Here, the illumination system is designed as a compact module, and so it can be easily combined with other measurement systems, without colliding with the beam paths thereof.

BRIEF DESCRIPTION OF THE DRAWINGS

The invention is described in more detail below on the basis of exemplary embodiments. In the figures.

DETAILED DESCRIPTION

Example embodiments of an illumination system for determining the topography of the cornea of an eye consists of include an illumination unit and a unit for producing an illumination pattern. Here, the illumination unit consists of a plurality of illumination modules. A lens array which produces a spatially distributed, collimated illumination pattern is used as a unit for producing an illumination pattern.

In contrast to the lens arrays generally known from the literature, which consist of converging lenses with a positive focal length, the example lens array employed here consists of diverging lenses with a negative focal length.

According to the invention, the illumination unit consists of, for example, at least two illumination modules, in another example embodiment, four illumination modules and in a further example embodiment, six or more illumination modules, which ensure a full-area illumination of the unit for producing an illumination pattern. To this end, the illumination modules are arranged in such a way that the illumination light of each illumination module illuminates part of the unit for producing an illumination pattern.

In addition to a light source, each illumination module comprises at least one reflective or refractive optical element for imaging the light source into the eye.

Different variants of the solution according to example embodiments of the invention are explained in more detail below on the basis of graphical illustrations.

Figure 1:
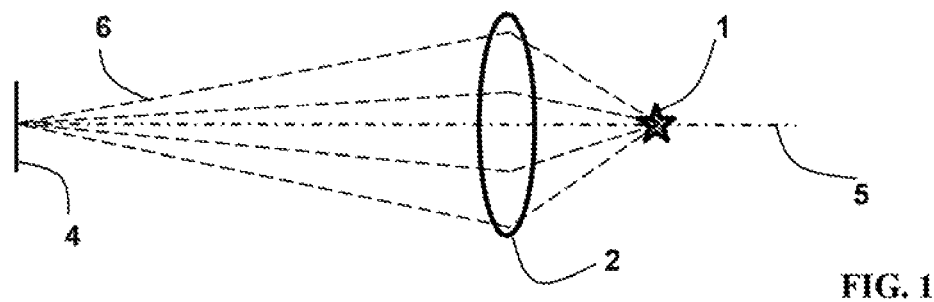
FIG. 1: depicts the beam path for imaging a light source into the eye.

According to a first example configuration each illumination module comprises an imaging optical element in addition to a light source in order to image the light source into the eye via the lens array. In addition to aspheres, Fresnel lenses or concave mirrors can also be used as an imaging optical element. To this end, FIG. 1 shows the beam profile for imaging a light source into the eye without using the lens array according to the invention. The LED 1 is imaged into the eye situated in the plane 4 by the asphere 2. The optical axis of the illumination module is denoted by 5. The dashed line 6 shows the resultant beam profile.

On account of their small dimensions, LEDs are increasingly used as light sources. From a point with a large divergence angle, the light emanates from the light source and collects at an image point on the eye, which forms the symmetry point of all illumination modules.

Figure 2:
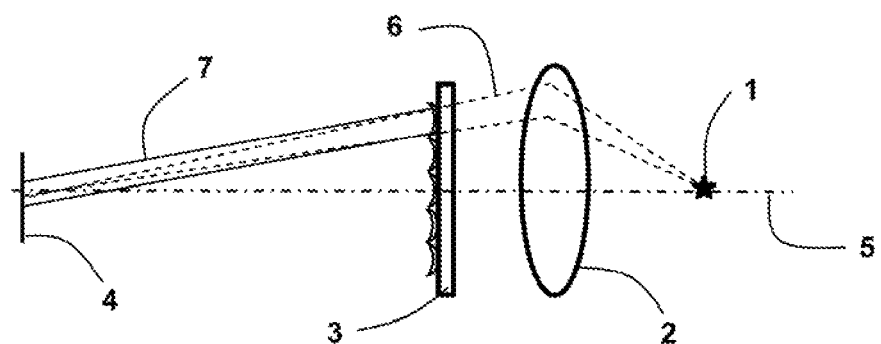
FIG. 2: depicts the beam path in an illumination module with an asphere.

To this end, FIG. 2 shows the beam profile in an illumination module with an asphere.

The LED 1 is imaged into the eye situated in the plane 4 by the asphere 2. The optical axis of the illumination module is denoted by 5. The dashed line 6 shows the beam profile without taking account of the lens array 3 that is arranged in the beam path and the full line 7 shows the beam profile when said lens array is taken into account. What can be gathered from FIG. 1 is that the rays 6 would intersect at a point in the plane 4 in which the eye is situated, whereas the rays along the line 7 were deflected by a lens of the lens array 3 and are incident on the eye in collimated fashion in plane 4. The collimated beams from different lenses of the lens array 3 differ in this case in terms of their angle of incidence on the plane 4. Instead of a single asphere, a plurality of lenses on the optical axis 5 can also be used for this imaging.

According to a second example configuration, each illumination module comprises a Fresnel lens in addition to a light source in order to image the light source into the eye via the lens array.

Figure 3:
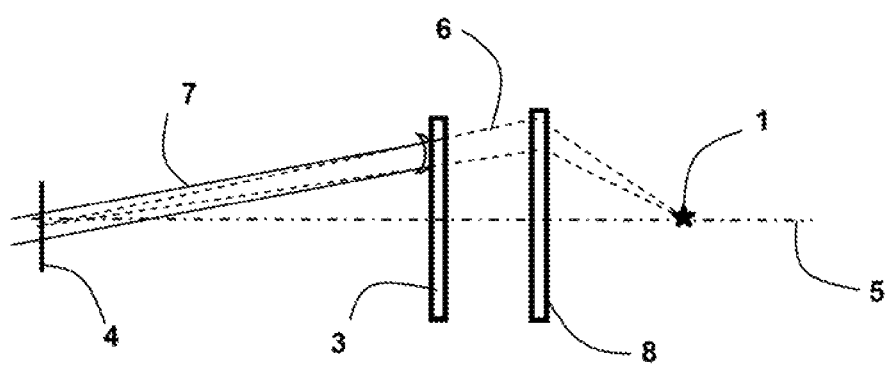
FIG. 3: depicts the beam path in an illumination module with a Fresnel lens.

FIG. 3 shows the beam path in an illumination module with a Fresnel lens.

The LED 1 is imaged into the eye situated in the plane 4 by the Fresnel lens 8. Once again, the dashed line 6 shows the beam profile without taking account of the lens array 3 that is arranged in the beam path and the full line 7 shows the beam profile when said lens array is taken into account.

The use of Fresnel lenses for example may be particularly advantageous to the effect that the weight of the overall structure, consisting of a Fresnel lens and a lens array, is substantially reduced. Both components can be embodied as plane, thin elements; as a result, they can easily be installed and can moreover be manufactured as injection molded parts.

According to a third example configuration, each illumination module comprises an elliptical reflector in addition to a light source in order to image the light source into the eye via the lens array. Here, the light source is situated in the first focus of the elliptical reflector and the eye is situated in the second focus thereof.

Figure 4:
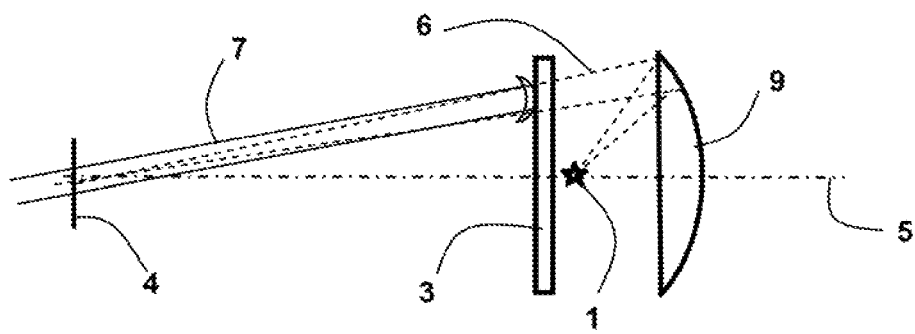
FIG. 4: depicts the beam path in an illumination module with an elliptical reflector.

To this end, FIG. 4 shows the beam profile in an illumination module with an elliptical reflector.

The LED 1 is imaged into the eye situated in the plane 4 by the elliptical reflector 9 via the lens array 3. Here, too, the dashed line 6 shows the beam profile without taking account of the lens array 3 that is arranged in the beam path and the full line 7 shows the beam profile when said lens array is taken into account.

This variant is moreover advantageous in that the LED can be arranged on the surface of the lens array facing the reflector, wherein the reflector can have an elliptical, aspherical, spherical or similar embodiment.

According to a further configuration, each illumination module may comprise a separate lens array.

Figure 5:
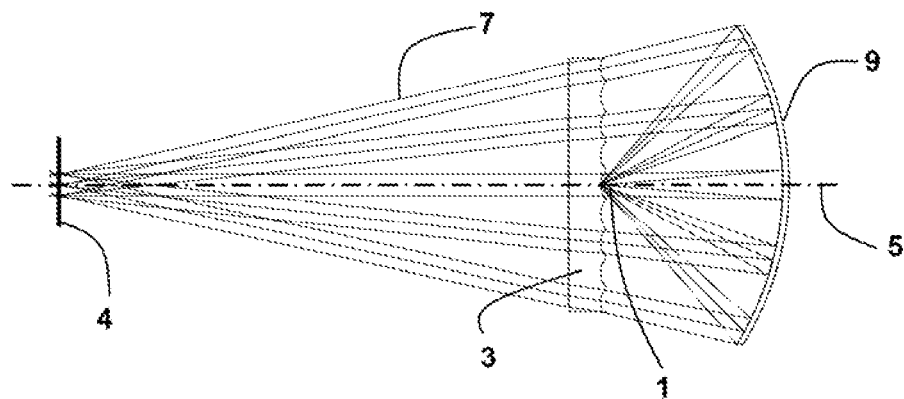
FIG. 5: depicts an illumination module with an elliptical reflector and a separate, planar lens array.
Figure 6:
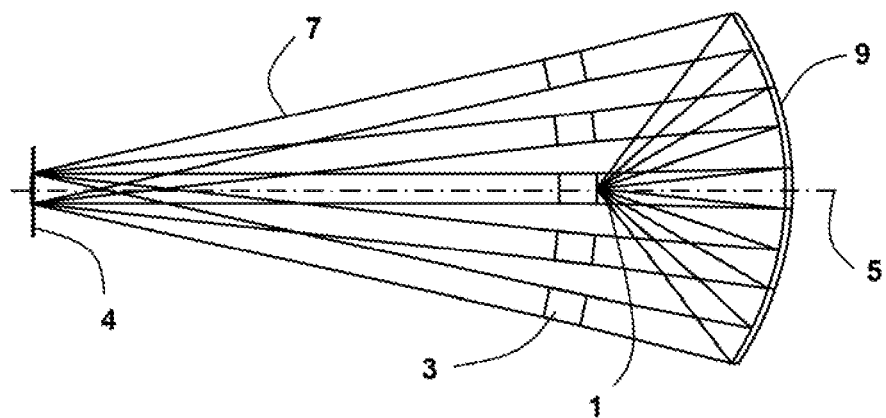
FIG. 6: depicts an illumination module with an elliptical reflector and a separate, concentric lens array.

FIGS. 5 and 6 show illumination modules with an elliptical reflector and a separate lens array.

While the illumination module of FIG. 5 comprises a plane lens array, FIG. 6 shows an illumination module with an elliptical reflector and a concentric lens array.

According to a further example embodiment of the illumination module that is described in FIG. 5 with an elliptical reflector, the lens array has identical individual lenses on a plane carrier, wherein the axes thereof extend parallel to one another and perpendicular to the substrate. As a result, such an illumination module is able to be manufactured particularly easily.

An example configuration of the solution according to FIG. 6 likewise provides for the use of identical individual lenses with the same focal lengths or external radii. However, a spherical carrier is used in this case. The optical axes of all individual lenses extend perpendicular to the carrier and hence concentric to the eye.

According to example embodiments of the invention, the individual lenses of the lens array are arranged in a rectangular, radially symmetrical or hexagonal grid on a planar or spherical surface that is concentric to the eye and are designed in such a way that the spatially distributed illumination pattern to be produced is produced by refracting the illumination light. In so doing, a collimated partial beam arises for each individual lens, said partial beam having the diameter of the microlens array.

Now, a multiplicity of partial beams arise as a result of the multiplicity of microlenses, said partial beams each extending in collimated fashion. Each partial beam illuminates the eye from a different angle, and so the desired illumination pattern arises.

In the case of the plane lens array, as illustrated in FIG. 5, all individual lenses have the same focal length and an optical axis that lies perpendicular to the plane surface. Consequently, the individual lenses in the lens array have the same external contour and the same optical properties such as focal length, radius of curvature, refractive index and optical axis, but are illuminated at different angles which are produced in the imaging element. Then, a multiplicity of collimated beams that meet on the eye arise in the overall arrangement.

If use is made of a concentric lens array according to FIG. 6, the individual lenses of the lens array are aligned in such a way that the optical axes thereof intersect at a common center in the eye. Hence, the lenses in the lens array lie with central symmetry about the common point of intersection. They can both have a biconcave embodiment, or else, as illustrated, have a common concentric base area and have a concave embodiment on the inner or outer side.

In order to obtain a common point of intersection of all beams in the eye, other imaging elements may also be used in combination with the concentric lens array, as already illustrated in FIGS. 2 to 5.

According to example embodiments of the invention, the individual lenses of the lens array have a negative focal length which, in terms of magnitude, deviates by, for example less than 15%, in another example by less than 10% and in a further example by less than 5% from the distance to the eye.

According to a further configuration, the individual lenses can be arranged on the side of the lens array facing away from the eye, wherein the basic form of the array lies concentrically around the optical axis.

As already mentioned, the lens array can have a spherical or else plane basic form, which lies concentric to the eye and the optical axis of the illumination system. Furthermore, the lens array can also be composed of a plurality of plane portions.

In an example embodiment, the lens array is able to be manufactured as an injection molded part. A plane basic form is merely distinguished by its simple manufacturability.

Figure 7A:
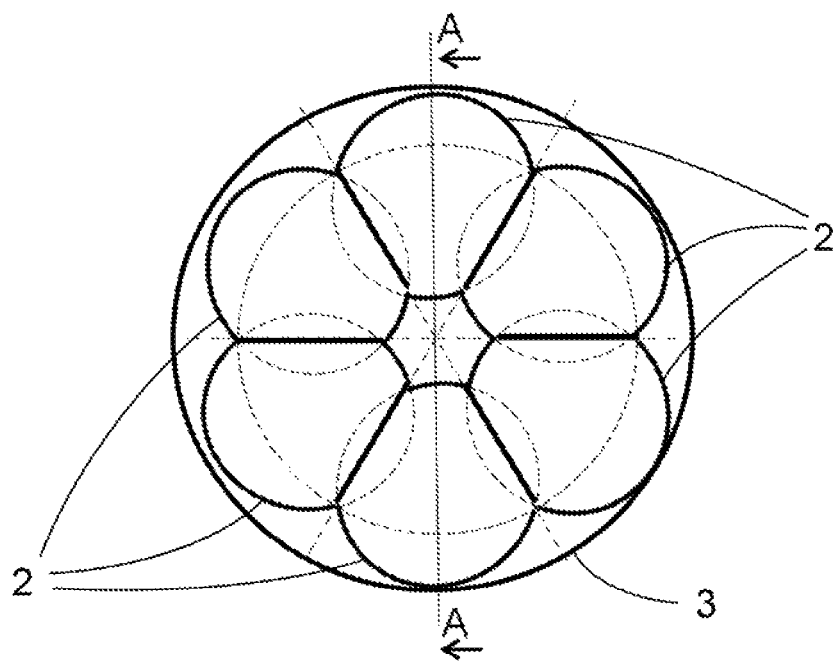
FIG. 7A: depicts an illumination system consisting of 6 illumination modules, having a lens array whose individual lenses are arranged on the side facing away from the eye.

To this end, FIG. 7A depicts an illumination system with 6 illumination modules, as is visible from the eye. The lens array 3 lies on a concentric surface facing the eye. The 6 illumination modules are arranged behind the lens array, which is embodied as aspheres 2 in this case.

Figure 7B:
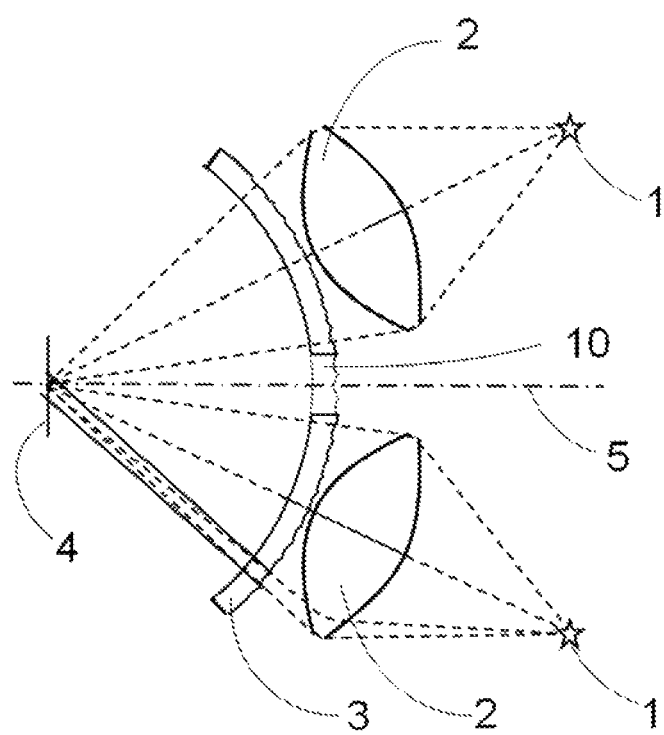
FIG. 7B: depicts a sectional illustration of the illumination system from FIG. 7B.

FIG. 7B shows the section through the illumination system from FIG. 7A. The lens array 3, whose individual lenses (as already illustrated in FIG. 5) are arranged on the side facing away from the eye, has a concentric arrangement with the eye. This is advantageous in that the front surface of the illumination system has a smooth surface which can easily be cleaned. It is consequently possible to dispense with an additional cover panel. The lens array 3 comprises a central opening 10 for other beam paths, such as a telecentric detection beam path and/or the beam path for other tasks such as OCT or retina scanning, said central opening being situated on the axis of symmetry of the illumination system 11. A plurality of illumination modules with the optical axes 5 are arranged around this axes of symmetry 11.

For a possible configuration of the solution according to FIG. 7B, the illumination module is based on a lens array 3 with 472 microlenses with a trapezoidal external contour and an area of approximately 5×5 mm. By way of example, the employed lens array, which may consist of plastic or else glass, has an eye-facing radius of 80 mm. Then, the concave radius of the microlenses is likewise approximately 80 mm, and so a focal length of the microlenses of −80 mm arises. Advantageously, the eye-facing radius is greater than 40 mm, but particularly advantageously 80 to 150 mm. The module in FIG. 7B illuminates a full angle of approximately 90° +/−15% on the eye; however, it is also possible to choose a smaller full angle of 30 to 70 degrees.

Furthermore, the lens array may also be arranged on a plurality of plane portions, which each lie perpendicular to the optical axes 5.

By dividing the illumination unit into a plurality of illumination modules, the central region about the optical axis of the illumination system remains free for other beam paths and, furthermore, leads to the angles of incidence on the lens array remaining small.

The solution according to example embodiments of the invention provides an illumination system for determining the topography of the cornea of an eye, by use of which distance-independent measurements are possible. Since the region around the optical axis of the system is kept free, a telecentric, axially symmetric detection is possible. Furthermore, the partial beans incident on the eye in collimated fashion ensure a distance-independent illumination.

Moreover, a uniform brightness of the illumination pattern can be ensured by using a number of identical illumination modules.

The distribution of the illumination unit further leads to the focal lengths of the illumination modules being able to be reduced, and so the installation depth can be reduced.

The illumination system according to example embodiments of the invention for determining the topography of the cornea of an eye is furthermore connected with the following advantages:

- Installation space is kept free for the telecentric imaging of the light reflected at the cornea and further system components in the optical axis.
- Manufacturing costs are reduced by only using refractive surfaces in the arrays.
- The manufacture is optimized by reducing thickness differences as a consequence of smaller dimensions.
- The illumination modules have a reduced etendue.
- The tolerance sensitivity can be reduced.
- Optical elements for separating or superimposing illumination and measurement beam paths are dispensed with.
- Technology with a lower basic precision is employable, such as for example: hot stamping, injection molding, casting or the like.

The invention claimed is:

1. An illumination system for determining the topography of the cornea of an eye, comprising:
    an illumination unit that is configured to provide illumination outside of a central region surrounding an optical axis thereby enabling telecentric axially symmetric detection and a unit that produces an illumination pattern;
    wherein the illumination unit comprises a plurality of illumination modules, each of the plurality of illumination modules including a light source and at least one reflective or refractive optical element that images the light source toward the eye; and wherein the unit that produces the illumination pattern comprises a lens array which produces a spatially distributed, collimated illumination pattern outside of the central region.

2. The illumination system as claimed in claim 1, wherein the lens array comprises diverging lenses with a negative focal length.

3. The illumination system as claimed in claim 1, wherein the illumination unit comprises at least two of the illumination modules.

4. The illumination system as claimed in claim 3, wherein the illumination unit comprises at least four of the illumination modules.

5. The illumination system as claimed in claim 3, wherein the illumination unit comprises at least six of the illumination modules.

6. The illumination system as claimed in claim 1, wherein the illumination modules are arranged in such a way that the illumination light of each illumination module illuminates part of the unit for producing an illumination pattern.

7. The illumination system as claimed in claim 1, wherein each illumination module comprises at least one reflective or refractive optical element in addition to a light source to image the light source into the eye by way of the lens array.

8. The illumination system as claimed in claim 1, wherein each illumination module comprises an asphere as a refractive optical element in order to image the light source into the eye by way of the lens array.

9. The illumination system as claimed in claim 1, wherein each illumination module comprises a Fresnel lens as a refractive optical element to image the light source into the eye by way of the lens array.

10. An illumination system for determining the topography of the cornea of an eye, comprising:
    an illumination unit and a unit that produces an illumination pattern;
    wherein the illumination unit comprises a plurality of illumination modules; and the unit for producing an illumination pattern comprises a lens array which produces a spatially distributed, collimated illumination pattern;
    wherein each illumination module comprises an elliptical reflector as a reflective optical element to image the light source into the eye by way of the lens array, wherein the light source is situated at a first focus of the elliptical reflector and the eye is situated at a second focus of the elliptical reflector.

11. The illumination system as claimed in claim 1, wherein each of the illumination modules comprises a separate lens array.

12. The illumination system as claimed in claim 1, wherein the individual lenses of the lens array are arranged in a rectangular grid, a radially symmetric grid or a hexagonal grid on a spherical surface that is concentric with the eye.

13. The illumination system as claimed in claim 1, wherein the individual lenses of the lens array are arranged in a rectangular grid, a radially symmetric grid or a hexagonal grid on a plane surface.

14. The illumination system as claimed in claim 12, wherein the individual lenses of the lens array are aligned in such a way that the optical axes thereof intersect at a common center in the eye.

15. The illumination system is claimed in claim 1, wherein individual lenses of the lens array have a negative focal length which, in terms of magnitude, deviates by less than 15% from the distance between the cornea being illuminated and the lens array.

16. The illumination system is claimed in claim 15, wherein individual lenses of the lens array have a negative focal length which, in terms of magnitude, deviates by less than 10% from the distance between the cornea being illuminated and the lens array.

17. The illumination system is claimed in claim 15, wherein individual lenses of the lens array have a negative focal length which, in terms of magnitude, deviates by less than 5% from the distance between the cornea being illuminated and the lens array.

18. The illumination system as claimed in claim 11, wherein individual lenses are arranged on a side of the lens array facing away from the eye and a basic form of the lens array lies concentrically around the optical axis.

19. The illumination system as claimed in claim 1, wherein the lens array comprises an injection molded part.

* * * * *

UNITED STATES PATENT AND TRADEMARK OFFICE
CERTIFICATE OF CORRECTION

PATENT NO. : 11,298,015 B2
APPLICATION NO. : 16/330079
DATED : April 12, 2022
INVENTOR(S) : Beate Böhme et al.

It is certified that error appears in the above-identified patent and that said Letters Patent is hereby corrected as shown below:

In the Specification

Column 3, Line 48-49, delete "consists of"

Signed and Sealed this
Twenty-fourth Day of May, 2022

Katherine Kelly Vidal
*Director of the United States Patent and Trademark Office*